(12) United States Patent
Wang

(10) Patent No.: US 11,604,183 B2
(45) Date of Patent: Mar. 14, 2023

(54) LOW-NOISE BIOMOLECULAR SENSORS

(71) Applicant: Roche Sequencing Solutions, Inc., Pleasanton, CA (US)

(72) Inventor: Chao Wang, Tempe, AZ (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 879 days.

(21) Appl. No.: 16/478,438

(22) PCT Filed: Jan. 17, 2018

(86) PCT No.: PCT/US2018/014025
§ 371 (c)(1),
(2) Date: Jul. 16, 2019

(87) PCT Pub. No.: WO2018/136497
PCT Pub. Date: Jul. 26, 2018

(65) Prior Publication Data
US 2021/0132033 A1    May 6, 2021

Related U.S. Application Data

(60) Provisional application No. 62/447,861, filed on Jan. 18, 2017.

(51) Int. Cl.
*G01N 33/487*    (2006.01)
*G03F 7/09*    (2006.01)
(Continued)

(52) U.S. Cl.
CPC ....... *G01N 33/48721* (2013.01); *G03F 7/092* (2013.01); *G03F 7/11* (2013.01);
(Continued)

(58) Field of Classification Search
CPC .... H01L 21/0332; H01L 21/0337; G03F 7/11; G01N 33/48721
See application file for complete search history.

(56) References Cited

U.S. PATENT DOCUMENTS

2014/0002824 A1   1/2014   Kai et al.
2014/0374255 A1*  12/2014  Hongo ............... G01N 15/12
                                                   204/627
(Continued)

FOREIGN PATENT DOCUMENTS

WO    2015/127387 A1    8/2015
WO    2016/094131 A2    6/2016

OTHER PUBLICATIONS

Chen et al. ("The Formation of The Hexagonal Pyramid Facets on Wet Etching Patterned Sapphire Substrate", ECS Transactions, 50, (42) The Electrochemical Society; pp. 27-31; (Year: 2013).*

(Continued)

*Primary Examiner* — Binh X Tran
(74) *Attorney, Agent, or Firm* — Kilpatrick Townsend and Stockton LLP

(57) ABSTRACT

A method for forming a nanopore device includes providing a sapphire substrate and forming oxide layers on the front and back sides of the sapphire substrate. The oxide layer on the back is patterned to form an etch mask. The method also includes performing a crystalline orientation dependent wet anisotropic etch on the backside of the sapphire substrate using the etch mask to form a cavity having sloped sides to expose a portion of the first oxide layer. A silicon nitride membrane layer is formed on the oxide layer on the front side of the sapphire substrate. Next, the exposed portion of the oxide layer in the cavity is removed to cause the exposed portion of the silicon nitride membrane layer to be suspended over the cavity in the sapphire substrate. Subsequently, an opening is formed in the suspended portion of the silicon nitride membrane layer to form the nanopore.

25 Claims, 13 Drawing Sheets

(51) Int. Cl.
- *G03F 7/11* (2006.01)
- *G03F 7/16* (2006.01)
- *G03F 7/36* (2006.01)
- *H01L 21/033* (2006.01)
- *B82Y 15/00* (2011.01)

(52) U.S. Cl.
CPC ................ *G03F 7/167* (2013.01); *G03F 7/36* (2013.01); *H01L 21/0332* (2013.01); *H01L 21/0337* (2013.01); *B82Y 15/00* (2013.01)

(56) References Cited

U.S. PATENT DOCUMENTS

2014/0374695 A1* 12/2014 Astier ............... B01L 3/502707
  438/49
2017/0058336 A1* 3/2017 Ivankin ................ C12Q 1/6869

OTHER PUBLICATIONS

International Search Report and Written Opinion in PCT/US2018/014025 dated May 23, 2018; 17 pages.

Deng, T. et al.; "Fabrication of Inverted-Pyramid Silicon Nanopore Arrays with Three-Step Wet Etching"; *ECS Journal of Solid State Science and Technology*; vol. 2, No. 11, Aug. 7, 2013; pp. P419-P422.

\* cited by examiner ly on the electrical properties of the nanopore device. Therefore, there is a need for improved nanopore device design and methods for controlling nanopore fabrication in a manner suitable for mass production.

LOW-NOISE BIOMOLECULAR SENSORS

CROSS-REFERENCE TO RELATED PATENT APPLICATIONS

This application is a US National Phase Application Under 371 of PCT Application No. PCT/US2018/014025 filed Jan. 17, 2018, which claims benefit of priority to U.S. Provisional Patent Application No. 62/447,861, filed on Jan. 18, 2017, each of which is incorporated by reference for all purposes.

BACKGROUND OF THE INVENTION

Nanopore-containing devices have use in biomolecular sensing. For example, nanopores may be used for nucleic acid sequencing. Conventional nanopore-based devices usually contain protein nanopores inserted in metastable lipid bilayers. The lipid bilayers may be fragile and may undermine the stability of the devices.

Compared with conventional biological DNA sequencing technologies, solid-state nanofluidic DNA sensors are relatively robust, easy to operate, low-cost, and can be potentially integrated over a wafer scale using CMOS (Complementary Metal-Semiconductor-Oxide-Silicon) integrated circuit processes. FIG. 1 is a simplified cross-sectional view diagram illustrating part of a conventional solid state nanopore sensor. In FIG. 1, a silicon (Si) based nanopore sensor 100 includes a silicon substrate 110 and a dielectric layer (e.g. silicon nitride, or $Si_3N_4$) 120 formed on the silicon substrate. A nanopore 130 is formed in the dielectric layer. The solid state nanopore forms a channel in an ionic liquid between two electrodes 161 and 162. As a biomolecule 140, e.g., a nucleic acid molecule, passes though the nanopore channel, the current and other electrical characteristics through the channel change. These electrical characteristics can provide information about the components of the molecule, e.g., a sequence of a nucleic acid molecule.

On the other hand, the differentiation of biomolecules relies strongly on the electrical properties of the nanopore device. Therefore, there is a need for improved nanopore device design and methods for controlling nanopore fabrication in a manner suitable for mass production.

BRIEF SUMMARY

The silicon-based nanopore device configuration is popular because of its high-throughput, high precision, low cost, and easy integration with existing manufacturing technologies. However, one inherent problem with the Si-based nanopore devices is the large noise in the detected signals as described further below. Embodiments of the present invention provide a low-noise nanopore structure in a sapphire substrate for biomolecular sensors and a method of creating low-noise nanopores by controlled wet-etching of a sapphire substrate. This process can reduce the noise of biomolecular sensors.

Compared with conventional nanopores formed in Si substrates, the use of a sapphire substrate greatly reduces the parasitic capacitance, hence greatly reducing current noise and extending bandwidth. There have been reports of using insulating fused silica substrate for nanopores. However, such a method requires complicated processes such as lengthy dry etching or polishing of fused silica substrate, which are usually single-wafer processes and are not scalable to large-scale manufacturing. In some embodiments of the invention, wet etching is used to form the sapphire structure and is compatible with batch processing for greater throughput. In some embodiments, the nanopores are formed in a dielectric membrane disposed over the sapphire substrate.

According to some embodiments of the invention a method for forming a nanopore device includes providing a sapphire substrate, and forming a first oxide layer on a front side of the sapphire substrate and a second oxide layer on a back side of the sapphire substrate. The second oxide layer is patterned to form an etch mask having a mask opening in the second oxide layer. The method also includes performing a crystalline orientation dependent wet anisotropic etch on the backside of the sapphire substrate using the etch mask to form a cavity having sloped side walls through the sapphire substrate to expose a portion of the first oxide layer. Each of the sloped side walls is a crystalline facet aligned with a respective crystalline plane. Then, a silicon nitride membrane layer is formed on the first oxide layer on the front side of the sapphire substrate. Next, the exposed portion of the first oxide layer in the cavity is removed to expose a portion of the silicon nitride membrane such that the exposed portion of the silicon nitride membrane layer is suspended over the cavity in the sapphire substrate. Subsequently, an opening is formed in the suspended portion of the silicon nitride membrane layer to form the nanopore.

In some embodiments, both the front side and the back side of the sapphire substrate are configured in c-planes of the sapphire substrate. In other words, both the front side and the back side of the sapphire substrate are characterized by a c-plane orientation. The mask opening in the etch mask can be triangular-shaped, and each of three sides of the triangular-shaped mask opening is aligned with a hexagonal crystalline orientation of the sapphire substrate. In a specific example, the etch mask has a triangular-shaped mask opening, and each of three sides of the triangular-shaped mask opening is aligned parallel to a crystalline plane in the sapphire substrate or forms a 60° or 120° angle from said crystalline plane in the sapphire substrate. The mask opening in the etch mask can also have a polygon shape.

According to some embodiments of the invention, a method for forming a nanopore device includes providing an insulating substrate having a crystalline orientation dependent wet etching selectivity. The method also includes forming a first dielectric layer on a front side of the insulating substrate and a second dielectric layer on a back side of the insulating substrate. The second dielectric layer on the backside of the insulating substrate is patterned to form an etch mask having a mask opening in the second dielectric layer. Next, a wet anisotropic etch is performed on the backside of the insulating substrate using the etch mask to form a cavity that extends through the insulating substrate to expose a portion of the first dielectric layer. A membrane layer is then formed on the first dielectric layer on the front side of the insulating substrate. Next, the exposed portion of the first dielectric layer in the cavity is removed such that a portion of the membrane layer is suspended over the cavity in the insulating substrate. Subsequently, an opening is formed in the suspended portion of the membrane layer to form the nanopore.

In some embodiments, the cavity has sloped sidewalls through the insulating substrate to expose a portion of the first dielectric layer. The cavity can be configured to extend from a first opening in the back side of the insulating substrate to a second opening in the front side of the insulating substrate. The second opening is smaller than the first opening, and sidewalls extending from the first opening to the second opening are characterized by crystalline orientations determined by the wet anisotropic etch.

According to some embodiments of the invention, a nanopore device for analyzing biological molecules includes a nanopore disposed in a membrane overlying a sapphire substrate, a first fluidic reservoir and a second fluidic reservoir fluidically coupled to the nanopore. The device has first and second electrodes coupled to an electrically conductive fluid disposed in the first and second reservoirs, respectively, and an electrical measuring device for measuring an electrical signal between the first and second electrodes. In an embodiment, the nanopore device is configured to apply an electrical voltage between the first and second electrodes and measure a current signal between the first and second electrodes. In an alternative embodiment, the nanopore device is configured to apply an electrical current between the first and second electrodes and measure a voltage signal between the first and second electrodes. In an embodiment, a cavity is formed by a wet anisotropic etch of the sapphire substrate, and the membrane is suspended over the cavity in the sapphire substrate. In a specific embodiment, the cavity is configured to extend from a first triangular opening in a back side of the sapphire substrate to a second triangular opening in a front side of the sapphire substrate, the second triangular opening being smaller than the first triangular opening.

A further understanding of the nature and advantages of the present invention may be realized by reference to the remaining portions of the specification and the drawings

DETAILED DESCRIPTION

Embodiments of the present invention provide a method for forming a low-noise nanopore sensor in a thin membrane suspended on an insulating substrate, for example, a sapphire substrate. Sapphire is a variety of the mineral corundum, also known as aluminum oxide ($Al_2O_3$). Corundum crystal is usually illustrated using hexagonal axes, as described in further detail with reference to FIGS. 6A and 6B. Commercial sapphire semiconductor substrates are often manufactured by the Czochralski crystal growth process, in which a thin seed of sapphire with precise crystal orientation is dipped into molten sapphire and is slowly pulled from the melt to allow the crystal to grow. In the semiconductor industry, thin sapphire wafers are used as an insulating substrate upon which a crystalline silicon layer is formed to make the integrated circuits known as silicon on sapphire or "SOS".

In embodiments of the invention, using a crystalline insulating substrate having a wet etching selectivity that is crystalline orientation dependent, for example, an insulating sapphire substrate in a nanopore device can greatly reduce the parasitic capacitance associated with the nanopore devices and thus the current noise, which are critical to biomolecule detection at low-current levels. In some embodiments, the manufacturing method of such nanopore devices on sapphire includes using controlled anisotropic wet etching, in which the etch rates are dependent on the crystal orientation of sapphire and hence can precisely control the membrane size by the design of an etching mask. Insulating materials, such as silicon oxide, silicon nitride, etc., have been used as the membrane layer in which the nanopore is formed. However, in solid state nanopore devices, the supporting substrate is usually formed with a silicon substrate, which a semiconductor. Other insulating substrates could be used, such as fused silica, but compared with sapphire, they do not have the superior electrical properties and crystalline orientation dependent etch selectivity that can be used to precisely define the membrane size and shape. Other insulating crystalline materials may be used, particularly ones having orientation dependent etch selectivity. In addition, wet etching of sapphire substrates can have a high etching rate of 0.1 μm to 1 μm per minute, allowing etching through the thickness of the sapphire wafer at a high throughput. Compared with dry etching processes that require extensively long etching time and single-wafer processing, wet etching is compatible with large-volume batch production, hence allowing high throughput production of high-sensitivity nanopore sensors at a low cost. Additionally, the method provides a process and system that are compatible with conventional process technology without substantial modifications to conventional equipment and processes.

I. Sapphire Substrate Based Nanopore Devices for Biomolecule Sensing

Figure 2:
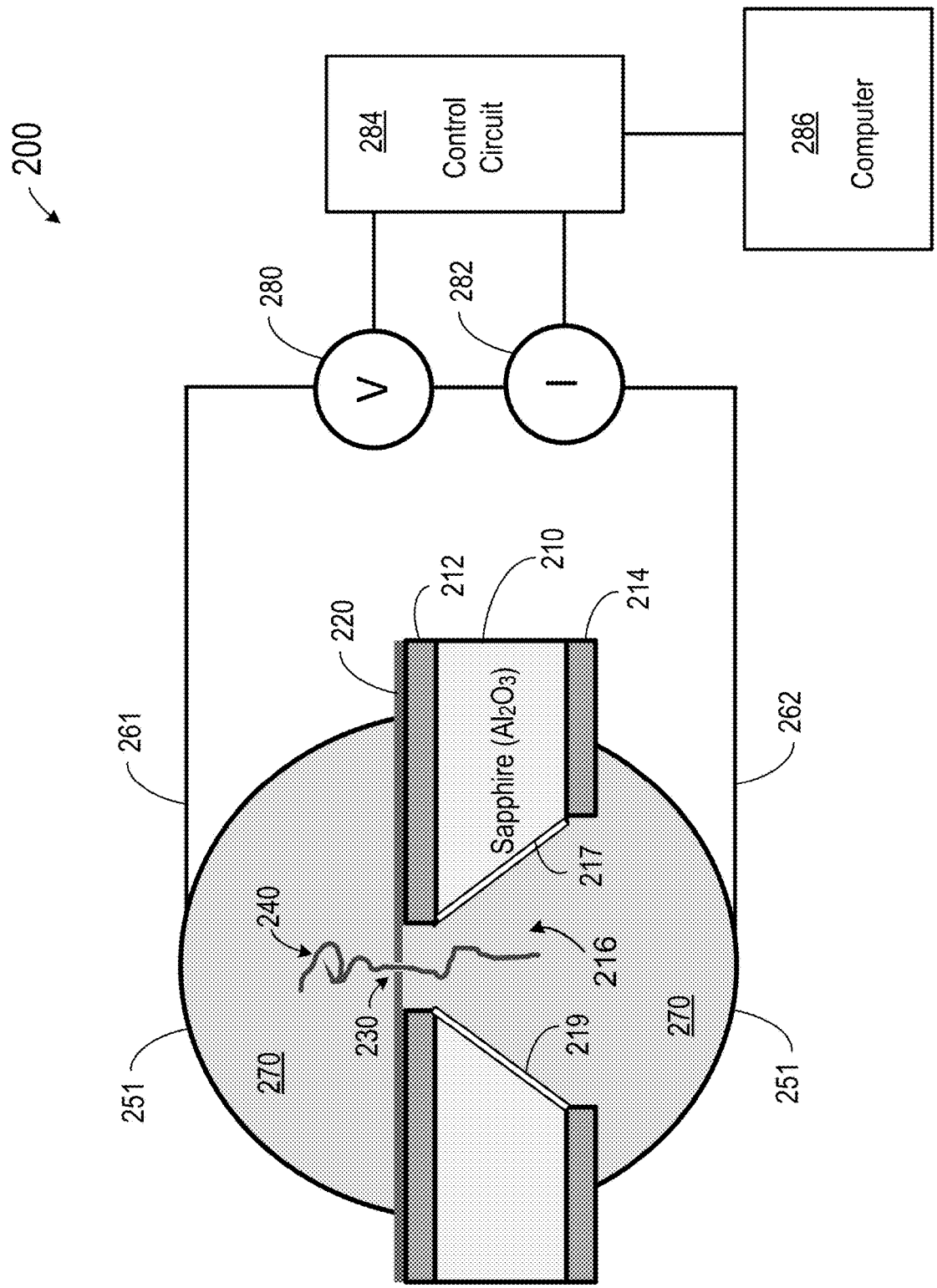
FIG. 2 is a simplified cross-sectional view diagram illustrating part of a solid state nanopore biomolecular sensor based on an insulating substrate according to some embodiments of the present invention.

FIG. 2 is a simplified cross-sectional view diagram illustrating part of a solid state nanopore biomolecular sensor based on an insulating substrate according to an embodiment of the present invention. In this embodiment, a sapphire substrate is used as an example of insulating substrates.

As shown in FIG. 2, a nanopore device 200 for analyzing biological molecules includes a sapphire substrate 210, and dielectric layers 212 and 214 are disposed on top and bottom surfaces of sapphire substrate 210. A membrane 220 is disposed overlying top dielectric layer 212 on the sapphire substrate. A nanopore 230 is disposed in membrane 220. Sapphire substrate 210 includes a cavity 216. In some embodiments, a dielectric layer 219 is disposed on side surfaces 217 of cavity 216 in the sapphire substrate. A first fluidic reservoir 251 and a second fluidic reservoir 252 are fluidically coupled to nanopore 230.

A first electrode 261 and a second electrode 262 are coupled to an electrically conductive fluid 270 disposed in the first and second reservoirs. The electrodes are configured to impose an electrical potential difference from a voltage supply (V) 280 to conductive fluid 270. As a biomolecule 240 passes though the nanopore channel, it partially blocks the nanopore and thus changes the effective nanopore resistance. This results in a current amplitude change and can also modify the DNA translocation time through the nanopore. These electrical signals can be measured to provide genetic information on the molecule. Nanopore device 200 can also include a current measuring circuit (I) 282 for measuring the current through the nanopore. In this case, a constant voltage can be applied and current measured, which could be an instantaneous measurement or over a period of time (e.g., with an integrating capacitor). Alternatively, a constant current can be applied to the conductive fluid, and the voltage can be measured to determine changes in the resistance as a biomolecule 240 passes though the nanopore channel. In this case, component 282 (I) can represent a constant current supply, and component 280 (V) can represent a voltage measurement circuit. Further, both current and voltage can vary as well. As long as the current or voltage source is varied in a known or reproducible fashion, the measured electrical signals can be used to identify genetic information of the molecule. Nanopore device 200 can also have a control circuit 284 for controlling the measurement for processing the detected signal. Control circuit 122 may include amplifier, integrator, noise filter, feedback control logic, and/or various other components. Control circuit 122 may be further coupled to a computer 286 for analyzing the signals to determine the components of the molecule, e.g., bases of a DNA molecule.

II. Analysis of Measurement Noise Caused by Parasitic Capacitance

Replacing the conductive Si substrate with an insulating substrate can minimize parasitic capacitances and reduce the current noise and improve the detection sensitivity. To demonstrate the benefits of using an insulating substrate, such as a sapphire substrate, the device capacitance is estimated as follows.

Figure 3B:
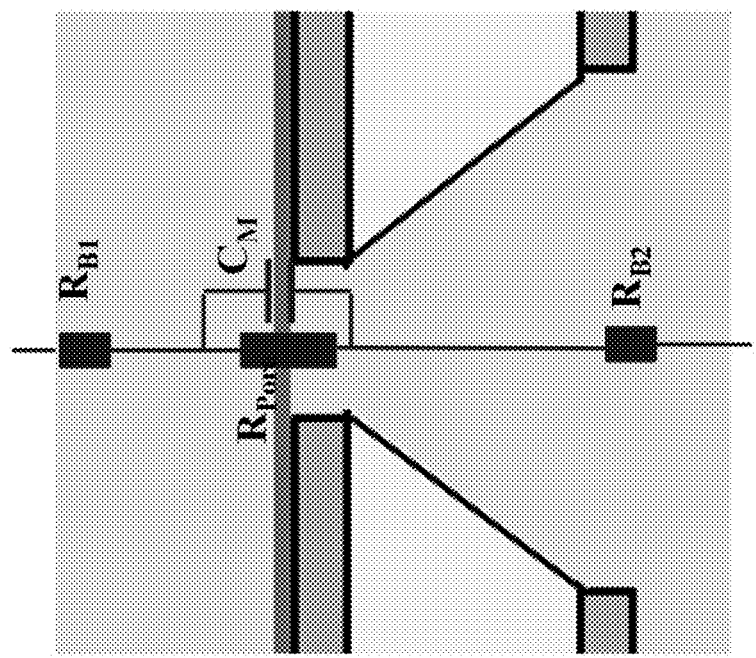
FIG. 3B is a simplified schematic diagram illustrating an equivalent circuit for the nanopore device 200 having a sapphire substrate of FIG. 2.
Figure 3A:
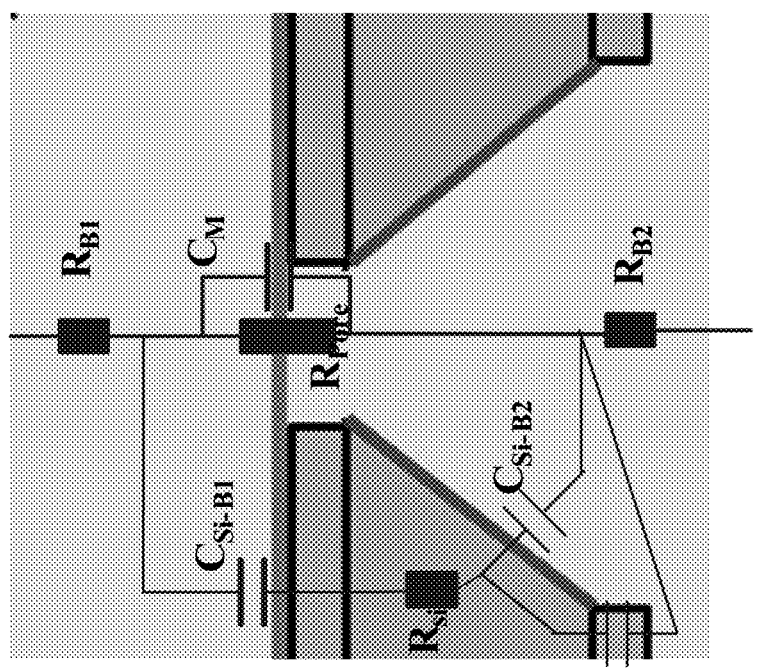
FIG. 3A is a simplified schematic diagram illustrating an equivalent circuit for a nanopore device having a silicon substrate.

FIG. 3A is a simplified schematic diagram illustrating an equivalent circuit for a nanopore device having a silicon substrate, and FIG. 3B is a simplified schematic diagram illustrating an equivalent circuit for the nanopore device 200 having a sapphire substrate of FIG. 2. In FIGS. 3A and 3B, the following symbols represent the equivalent resistances or capacitances in the nanopore devices.

$R_{B1}$—the equivalent resistance of the conductive fluid in the first fluidic reservoir;
$R_{B2}$—the equivalent resistance of the conductive fluid in the second fluidic reservoir;
$R_{Pore}$—the equivalent resistance of the nanopore;
$R_{si}$—the equivalent resistance of the silicon substrate;
$C_M$—the equivalent capacitance of the membrane;
$C_{Si-B1}$—the equivalent capacitance between the silicon substrate and the conductive fluid in the first fluidic reservoir; and
$C_{Si-B2}$—the equivalent capacitance between the silicon substrate and the conductive fluid in the second fluidic reservoir.

As described above, one inherent problem with the Si-based nanopore devices is the large noise caused by the silicon substrate being a semiconductor. The large noise stems from large parasitic capacitances, $C_{Si-B1}$ and $C_{Si-B2}$, resulted from the charges at the Si surfaces responding to the external voltage supply. The noise seriously limits the minimal current signal difference that can be distinguished, and also limits how fast the current modulation can be detected. These limitations lower the signal bandwidth, which is a measure of the width of a range of signal frequencies that can be handled by an electronic device. Despite efforts to minimize the noise, the substrate related capacitances remains a challenge that blocks further improvement of the sensitivities of such nanopore devices for single-molecule DNA base sequencing.

To estimate the parasitic capacitance, FIG. 3A illustrates key capacitances of the membrane and the parasitic capacitances. Assuming a membrane of $SiO_2$ with a thickness of 20 nm and an area of 10 μm by 10 μm, its membrane capacitance $C_M$ is about 0.2 pF, using the following relationship.

$$C_M = \epsilon_d \frac{A_M}{t_M} = 0.2 \text{ pF } (0.17 \text{ pF})$$

The nanopore resistance $R_{Pore}$ can be determined as follows. Assuming 1 M KCl (potassium chloride) (conductivity $10^5$ μS/cm), nanopore diameter 5 nm.

$$R_{pore} = \frac{1}{\sigma} \frac{t_M}{A_{pore}} = 10^8 \text{ Ohm}$$

The buffer resistance RB can be determined as follows, assuming 1 M KCl (conductivity $10^5$ μS/cm), o-ring diameter of 5 mm and thickness of 1 mm.

$$R_B = \frac{1}{\sigma} \frac{t_{o-ring}}{A_{o-ring}} = 100 \text{ Ohm}$$

The parasitic capacitance of the thin dielectric layers on the front side of Si can be estimated as $$C_{Si-B1} = \epsilon_d \frac{A_{film}}{t_{film}}$$

which is about 9 nF assuming a 5 by 5 $mm^2$ chip surface and a 100 nm thick dielectric film. Additionally, the backside of Si inside the cavity is also coated with a thin layer of dielectric, which can result in another capacitance that is on the order of nano-farads. The total capacitance can be estimated to be about 5 nF.

The signal bandwidth and the noise of the current recordings are important parameters for nanopore sensing applications. For accurate measurements, the signal bandwidth must be sufficient to resolve fully the signal pulses. The nanopore noise current can be estimated by the following relationship, $$I = 2\pi / \sqrt{3}\, B^{\frac{3}{2}} (C_{total}) v_n$$

where $C_{total}$ is the total capacitance in parallel with the nanopore resistor, B is the bandwidth of detection, and $v_n$ is the voltage noise density (in the unit of $V/Hz^{1/2}$). It can be seen that the larger the $C_{total}$, the higher the current noise.

FIG. 3B is a simplified schematic diagram illustrating an equivalent circuit for the nanopore device 200 of FIG. 2. It can be seen that, because the sapphire is an insulator, the parasitic capacitances in FIG. 3A are removed in FIG. 3B. The only capacitance that remains is the membrane capacitance $C_M$, which is about 0.2 pF, using the same device parameters as those in FIG. 3A. Therefore, by replacing the conventional Si substrate with an insulating substrate, the total capacitance $C_{total}$ is reduced from about 5 nF to about 0.2 pF, resulting in more than four orders of magnitude reduction of noise.

On the other hand, the reduction of nanopore device capacitance also allows biomolecular detection at a higher bandwidth. High signal bandwidth, however, can also increase the noise of the current recordings; this noise limits the signal-to-noise ratio and hence the sensitivity of the pore because the amplitude of a signal pulse must be above the noise to be detectable. The maximum bandwidth to accurately detect a current change ΔI at a signal-to-noise ratio SNR can be estimated by the following equation, $$B_{max} = \frac{\Delta I \sqrt{3}}{SNR \times 2\pi (C_{total}) v_n}$$

Figure 1:
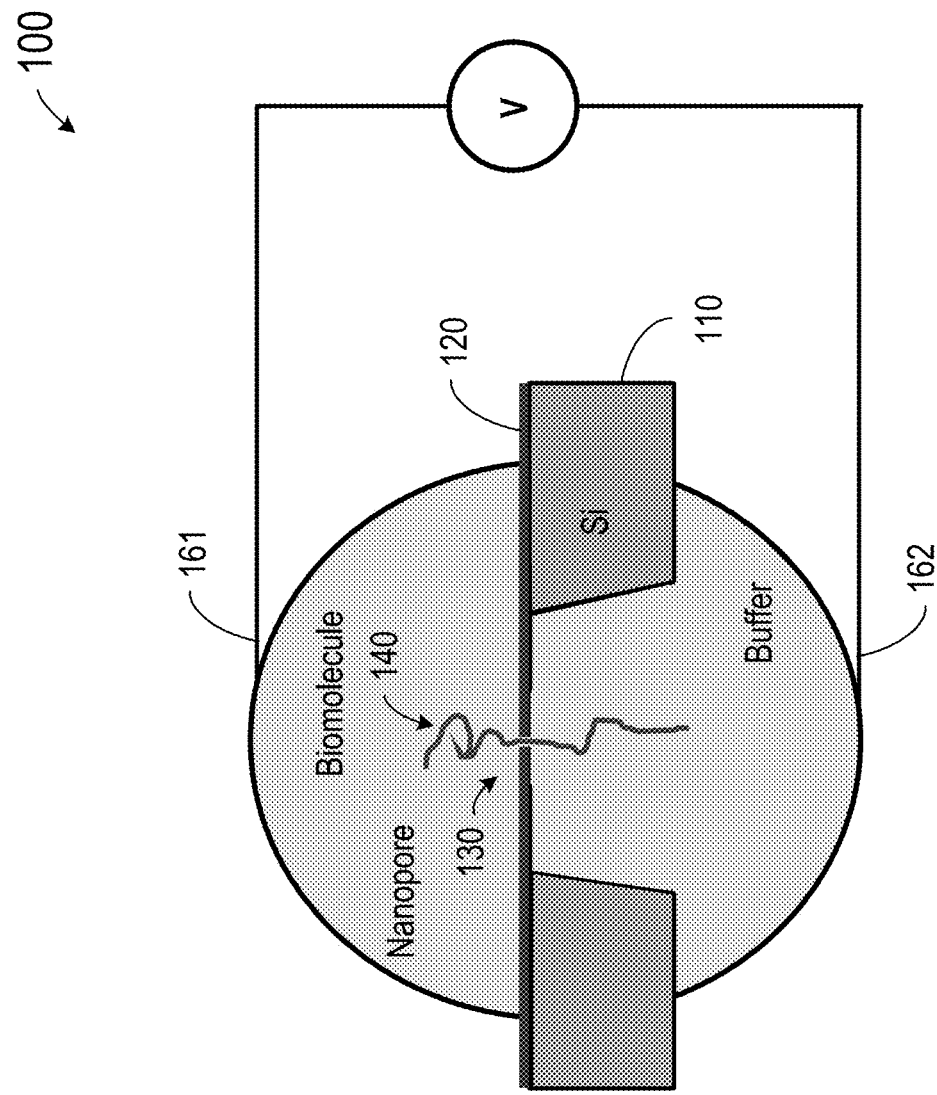
FIG. 1 is a simplified cross-sectional view diagram illustrating part of a conventional solid state nanopore sensor.

It can be seen that the reduction of membrane capacitance can significantly improve the bandwidth. Using the examples in FIGS. 1B and 2B, the bandwidth can be reduced by three to four orders of magnitude in the frequency range typically used for nanopore measurement (1 k to 1 M Hz)

III. Manufacturing of Nanopores on Insulating Substrates

Current manufacturing methods of nanopores on insulating substrates (e.g. glass) typically require melting the glass by laser and mechanical pulling in order to thin down the glass in specific locations. However, these methods are very time-consuming, expensive, not scalable, and not compatible with the Si manufacturing process. For these reasons, none of existing methods are suitable for large-scale nanopores on insulating substrates.

Embodiments of the present invention provide a method of forming dielectric membranes on insulating sapphire substrate, which is suitable to manufacture nanopore devices. The method can also be implemented using other crystalline insulating substrates having a wet etching selectivity that is crystalline orientation dependent. Embodiments can use an anisotropic chemical etching method to create cavities on a sapphire substrate. Typically, a mixture of sulfuric acid and phosphoric acid is heated to above 250 degrees and used for sapphire etching. This etching method results in selective etching c-plane sapphire much faster than other crystal planes. Using such an etching solution, a patterned material layer, e.g. made in $SiO_2$, can be used as an etch mask to effectively protect the sapphire underneath and hence creates a cavity in the region without this protective layer.

By precisely designing the shapes and dimensions of this protective layer (etching mask), embodiments can control the crystal facets on the sapphire substrates, and thus control the lateral dimensions of membrane precisely. This anisotropic wet etching is suitable for batch processing of multiple wafers for large-scale and low cost production, and thus hundreds and even thousands of nanopore membranes can be manufactured at the same time. The mask shape and dimensions can be precisely controlled, hence allowing precise high-yield production. In addition, the sapphire substrate is compatible with Si-based micro and nanofabrication technologies and can be further integrated with other electronic components.

A. Method of Manufacturing

Figure 4:
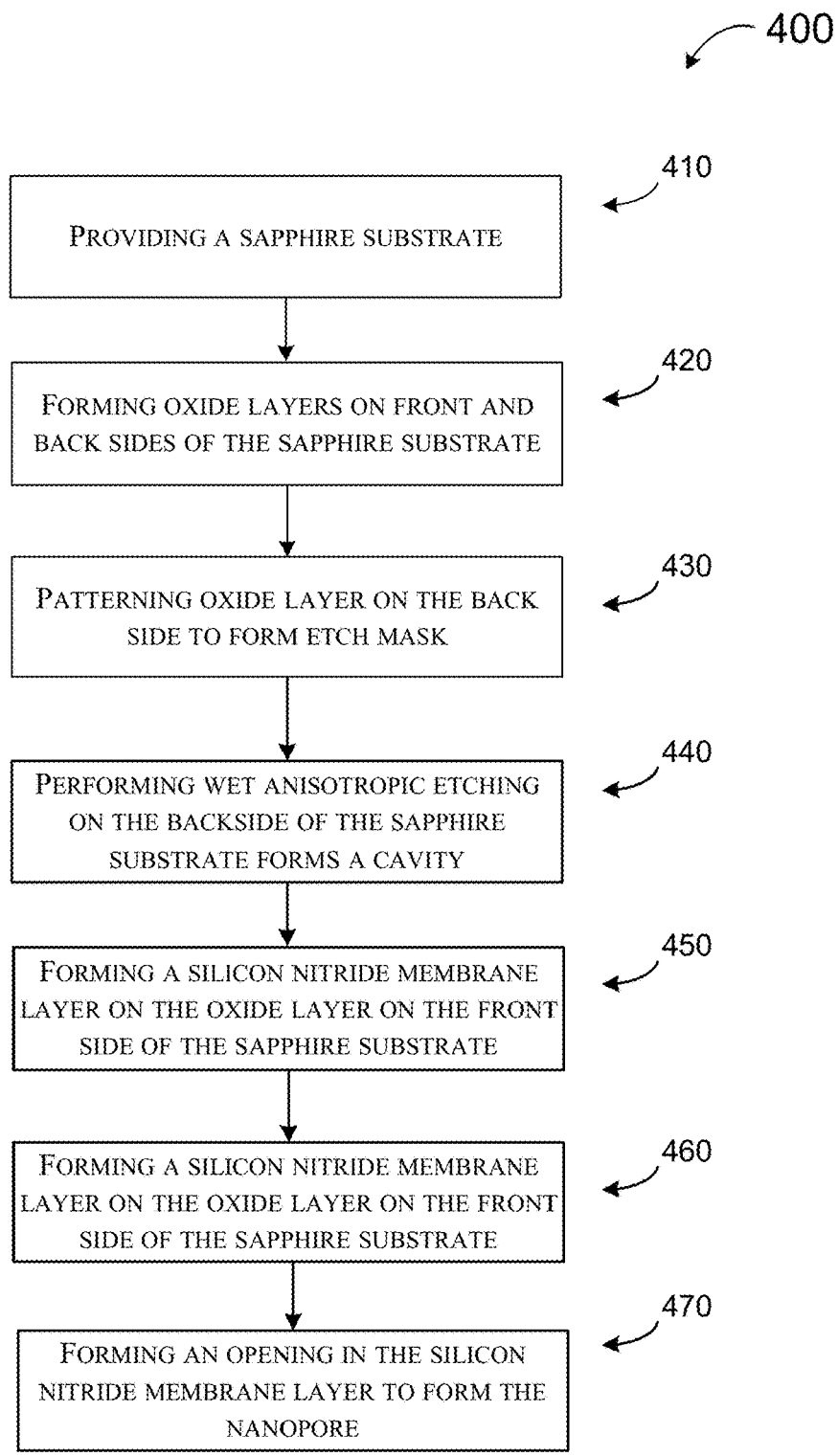
FIG. 4 is a flowchart illustrating a method for forming a nanopore device having a nanopore in a dielectric membrane on an insulating sapphire substrate according to some embodiments of the present invention.

FIG. 4 is a flowchart illustrating a method for forming a nanopore device having a nanopore in a dielectric membrane on an insulating sapphire substrate according to an embodiment of the present invention. The method is briefly summarized here and will be further described below with reference to FIGS. 5A-5G. As shown in FIG. 4, a method 400 forming a nanopore device includes the following steps.

Step 410: Providing a sapphire substrate;
Step 420: Forming oxide layers on front and back sides of the sapphire substrate;
Step 430: Patterning an oxide layer on the back side to form an etch mask;
Step 440: Performing wet anisotropic etching on the backside of the sapphire substrate to form a cavity;
Step 450: Forming a silicon nitride membrane layer on the oxide layer on the front side of the sapphire substrate;
Step 460: Removing the first oxide layer in the cavity such that the silicon nitride membrane layer is suspended over the cavity in the sapphire substrate; and
Step 470: Forming an opening in the silicon nitride membrane layer to form the nanopore.

FIGS. 5A-5G are simplified cross-sectional view diagrams illustrating the method for forming a nanopore device according to some embodiments of the present invention. The method is described below with reference to the flowchart in FIG. 4 and FIGS. 5A-5G. The same reference numerals are used in FIGS. 5A-5G to identify common components as the nanopore device 200 in FIG. 2.

Figure 5A:
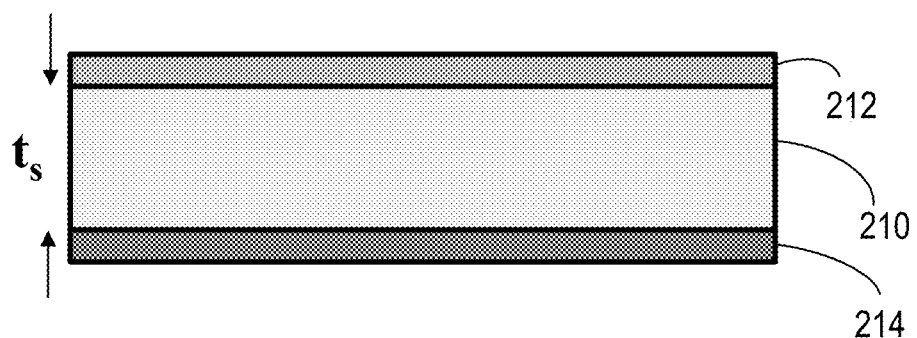
FIGS. 5A-5G are simplified cross-sectional view diagrams illustrating the method for forming a nanopore device according to some embodiments of the present invention.

At step 410 of method 400 in FIG. 4, a sapphire substrate 210 is provided as shown in FIG. 5A.

At step 420, as shown in FIG. 5A, a first dielectric layer 212 is formed on a front side of sapphire substrate 210, and a second dielectric layer 214 is formed on a back side of sapphire substrate 210. These dielectric layers can be made of the same material or different materials, and they can be deposited in the same process step or different steps. For example, the first dielectric layer 212 and the second dielectric layer 214 can both be a layer of silicon dioxide $SiO_2$. In some embodiments, a layer of silicon dioxide $SiO_2$ can be deposited on both sides of the sapphire wafer. Silicon dioxide $SiO_2$ is a chemical compound that is an oxide of silicon and is a common insulating or dielectric material used in the semiconductor industry.

The deposition can be carried by standard processes used in the semiconductor industry, such as low-pressure chemical vapor deposition (LPCVD), plasma enhanced chemical vapor deposition (PECVD), etc. In an LPCVD process, a silicon precursor, such as silane and an oxygen source, e.g., 02, are reacted in a low pressure system to form a layer of silicon oxide. In a PECVD process, the activation of plasma enables oxide deposition at lower temperatures. The thickness of such $SiO_2$ mask can be in a range of 10 nm to 10 μm, depending on the etching selectivity of the dielectric layers in subsequent etching steps. In the description below, the first dielectric layer 212 and the second dielectric layer 214 will be referred to as the first oxide layer 212 and the second oxide layer 214. It is understood that other dielectric materials can also be used.

Figure 5B:
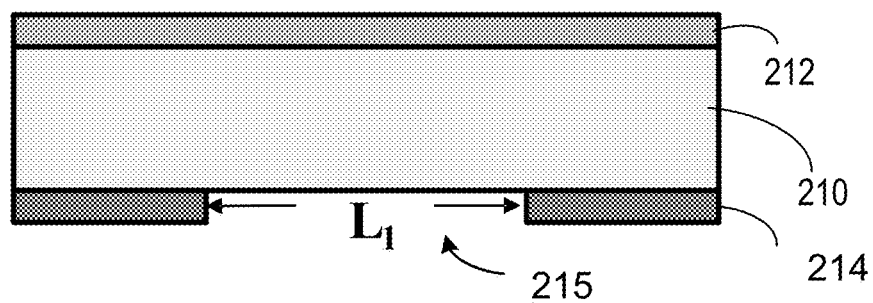

At step 430, as shown in FIG. 5B, the second oxide layer 214 on the backside of sapphire substrate 210 is patterned to form an etching mask having a mask opening 215 in the second oxide layer. The opening can be formed by an etching process using a patterned photoresist layer as a mask. First, photolithography is used to form a mask opening in a photoresist layer. Photolithography uses light to transfer a geometric pattern from a photomask to a light-sensitive chemical material layer (photoresist or resist) on a substrate. The exposure pattern enables the etching of the material underneath the photoresist.

Next, the $SiO_2$ layer can be etched by reactive ion etching (ME) with the patterned resist mask. As is known in the semiconductor industry, reactive-ion etching (ME) is a type of dry etching that uses chemically reactive plasma to remove material deposited on wafers. The plasma is generated under low pressure (vacuum) by an electromagnetic field. Under a high voltage, high-energy ions from the plasma attack the wafer surface. The ions can react chemically with the materials on the surface of the wafer, and can also knock off (sputter) some material. Due to the mostly vertical delivery of reactive ions, reactive-ion etching can produce anisotropic etch profiles, such as a vertical profile. In contrast, wet etching is a material removal process that uses liquid chemicals or etchants to remove materials from a wafer. The specific patters are defined by masks on the wafer. Materials that are not protected by the masks are etched away by liquid chemicals.

Unlike dry etching, wet etching is usually isotropic, i.e., the etch rate is the same in all directions. In embodiments of the invention, wet etching of the sapphire substrate is carried out using an anisotropic etching process in which the etch rate depends on the crystalline orientation. After the conclusion of the etch process, the photoresist is stripped using a standard process, e.g., by oxygen plasma ashing. In some embodiments, the mask opening can have a triangular-shaped window, such that all sidewalls of the cavity etched in a c-plane sapphire substrate, i.e., sapphire with (0111) orientation, are defined by crystalline facets after the crystalline orientation dependent etch. This design can lead to better etch profile control. Further, the triangular shaped opening can provide more mechanical stability. In FIG. 5B, the mask opening has a width of $L_1$, representing one side of the triangular-shaped window. As described below, the desired dimension of the membrane can be determined by the width of the mask opening.

Figure 5C:
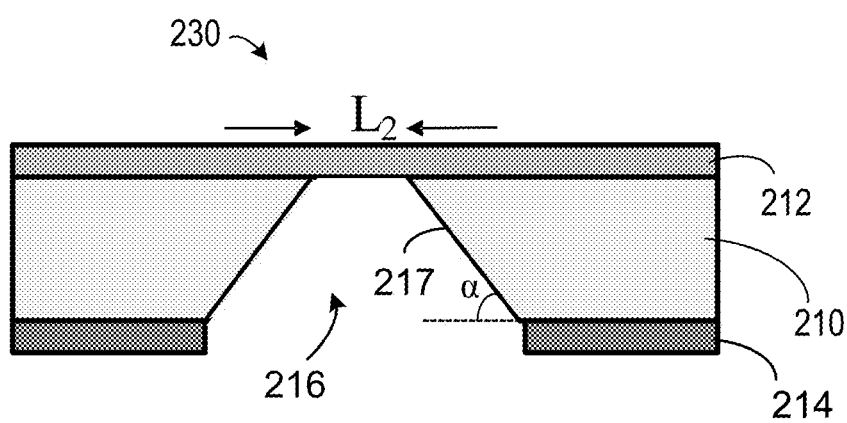

At step 440, as shown in FIG. 5C, the back side of the sapphire substrate is etched using the patterned etch mask to form a cavity 216. This etch is carried out using a wet anisotropic etch that has a crystalline orientation dependent etch selectivity. For example, wet etching of the sapphire can be performed in a mixture of sulfuric acid ($H_2SO_4$) and phosphoric acid ($H_3PO_4$) solutions at an elevated temperature, e.g., a temperature ranging from about 250° C. to about 300° C. Under these etching conditions, the etch rate of sapphire varies with the crystal orientation, and a preferential etching along certain crystalline planes can produce controlled etching profiles. The crystalline orientation dependent anisotropic etching of sapphire is described further below in connection with FIGS. 6A-10. As shown in FIG. 5C, cavity 216 has sloped sidewalls 217 through the sapphire substrate to expose a portion of the first oxide layer 212. The width of the exposed portion of first oxide layer 212 is designated as $L_2$.

Figure 5D:
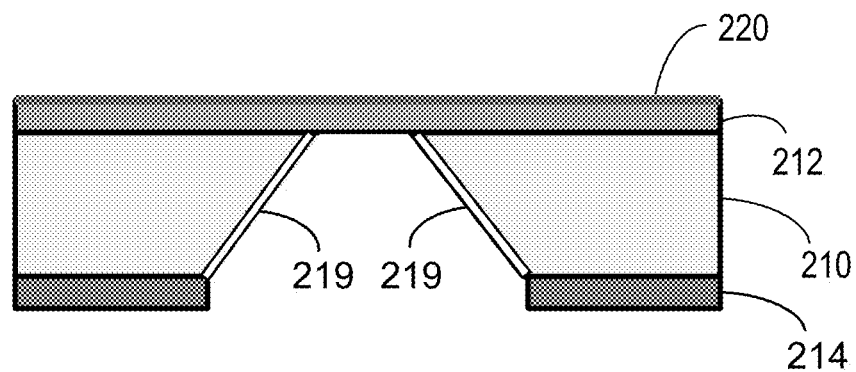

At step 450, as shown in FIG. 5D, a membrane layer 220 is formed on the first oxide layer 212 on the front side of the sapphire substrate. In order to further thin down the effective membrane thickness, a different dielectric material, e.g., silicon nitride ($Si_3N_4$), can be deposited on top of the on the first oxide layer 212. Silicon nitride films are a standard dielectric material in the semiconductor industry. A silicon nitride layer can be formed by a plasma enhanced chemical vapor deposition (PECVD) process as described above using silicon and nitrogen precursors. In some embodiments, the thickness of the silicon nitride layer can be from about 3 nm to about 50 nm. A silicon nitride ($Si_3N_4$) film and a silicon oxide ($SiO_2$) film can be etched using different wet or dry etch chemistries.

This etching selectivity allows one of the films to be used as a masking layer or an etch stop layer during the etching of the other film. In this example, silicon nitride layer 220 has a desirable etch selectivity with respect to the first oxide layer 212, and the $SiO_2$ can be selectively etched to leave the thin $Si_3N_4$ layer suspended on sapphire. In some embodiments, a protective layer 219, e.g., a dielectric layer, can be formed on the sidewalls of the cavity. To simplify the drawings, dielectric layers 219 will be omitted in some of the figures described below.

Figure 5E:
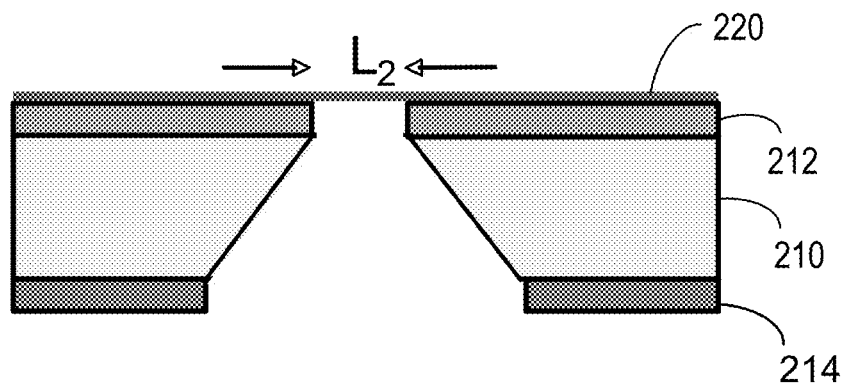

At step 460, as shown in FIG. 5E, the exposed portion of the first oxide layer in the cavity is removed. The first oxide layer can be etched using a fluorine based reactive ion etch (ME) process or a wet etch process using hydrofluoric acid (HF). Hydrofluoric acid is a solution of hydrogen fluoride (HF) in water and is a standard chemical for wet etching of silicon oxide. The exposed portion of the first oxide layer can be selectively etched without etching the silicon nitride layer. After the exposed oxide is removed, a portion of the silicon nitride membrane layer 220 is suspended over the cavity in the sapphire substrate. In the example of FIG. 5E, the width of the suspended portion of the membrane is shown as $L_2$.

Figure 5F:
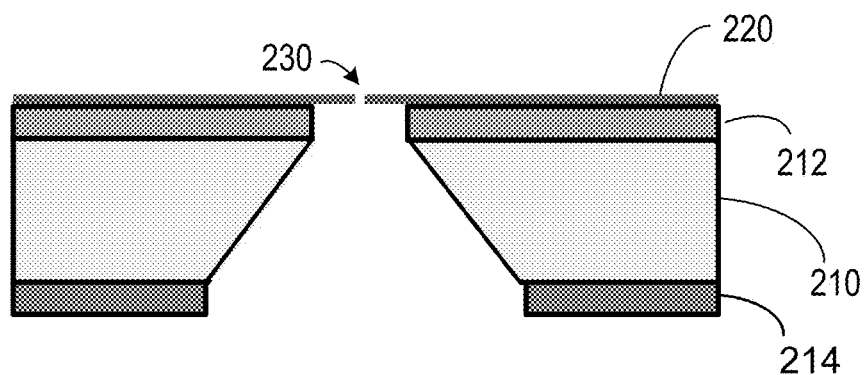

At step 470, as shown in FIG. 5F, a nanopore 230 is formed in the suspended portion of silicon nitride membrane layer 220. Nanopore 230 can be formed by RIE etching through an opening in a masking layer formed by nano-lithography such as photolithography or electron beam lithography. In some embodiments, the nanopore can have a size that is configured to allow one nucleic acid molecule to pass through the nanopore. Both photolithography and electron beam lithography can be used to create very small structures in the resist that can subsequently be transferred to the substrate material. Photolithography uses light to transfer a geometric pattern from a photomask to a light-sensitive chemical material layer referred to as a photoresist layer or a resist layer, on the substrate. The exposure pattern enables the etching of the material underneath the photo resist.

In electron-beam lithography, a focused beam of electrons is scanned to draw desired shapes on a surface covered with an electron-sensitive resist film. The electron beam changes the solubility of the resist, enabling selective removal of either the exposed or non-exposed regions of the resist by immersing it in a solvent in a developing process. The primary advantage of electron-beam lithography is that it can draw patterns (direct-write) with sub-10 nm resolution without using a mask. This form of maskless lithography has high resolution and low throughput. After the mask pattern is formed on the wafer, reactive ion etching can be used to form the nanopore. Alternatively, an opening can be formed in the silicon nitride film using focused electron beam etching to form the nanopore. In this maskless process, an electron beam is used to activate a chemical reaction in selected regions on a wafer to form a nanopore in the membrane film.

B. Nanopore Device

Figure 5G:
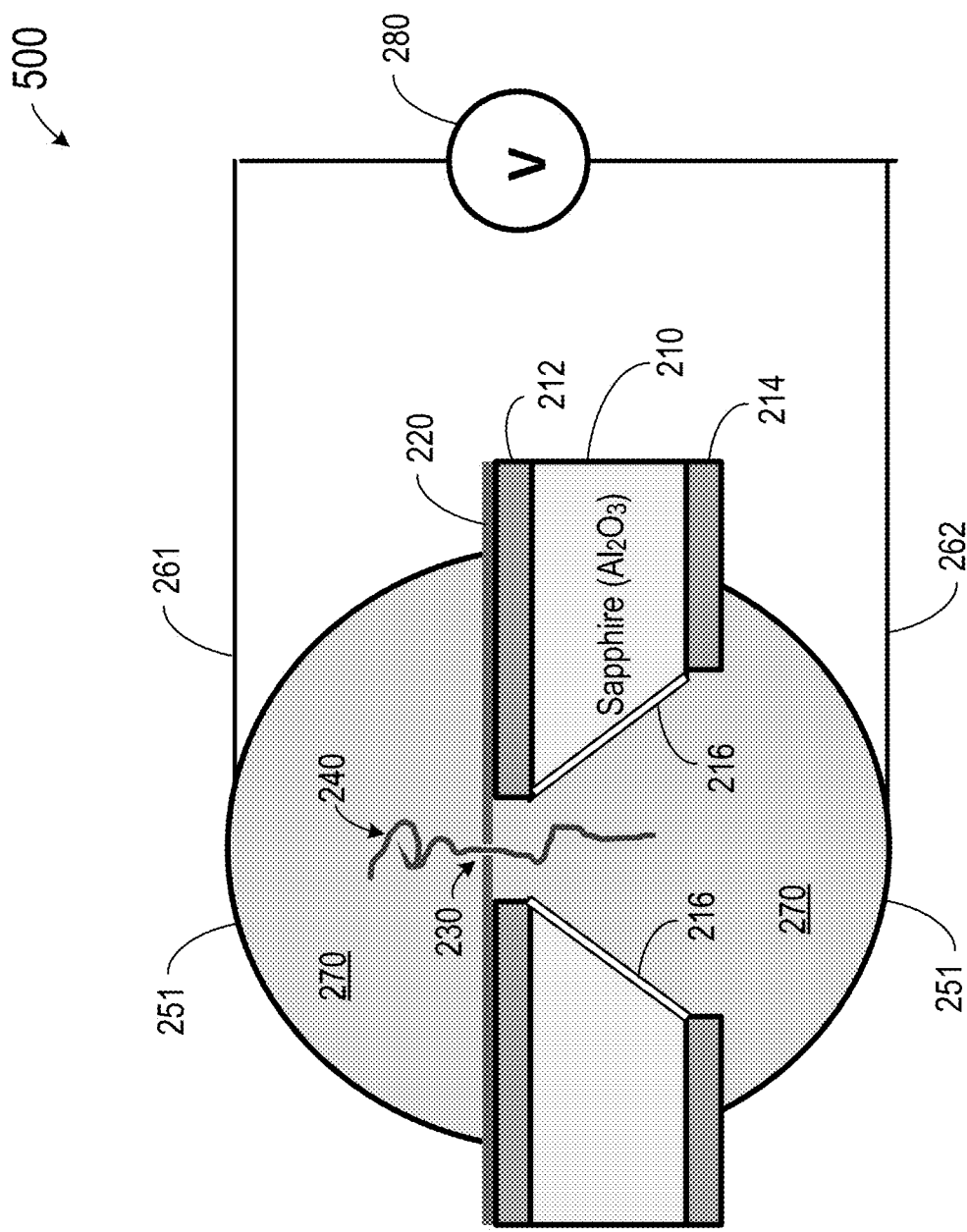

FIG. 5G is a simplified schematic diagram illustrating a nanopore device for analyzing biological molecules using a sapphire substrate based nanopore shown in FIG. 5F. As shown in FIG. 5G, a nanopore device 500 is similar to nanopore device 200 shown in FIG. 2. Nanopore device 500 includes a sapphire substrate 210, and dielectric layers 212 and 214 are disposed on top and bottom surfaces of sapphire substrate 210. A membrane 220 is disposed overlying top dielectric layer 212 on the sapphire substrate. A nanopore 230 is disposed in membrane 220. A dielectric layer 216 is disposed on the side surfaces of a cavity in the sapphire substrate. A first fluidic reservoir 251 and a second fluidic reservoir 252 are fluidically coupled to nanopore 230. A first electrode 261 and a second electrode 262 are coupled to an electrically conductive fluid 270 disposed in the first and second reservoirs. The electrodes are configured to impose an electrical potential difference from a voltage supply V 280 to conductive fluid 270. A biomolecule 240 is shown passing through nanopore 230.

Figure 5H:
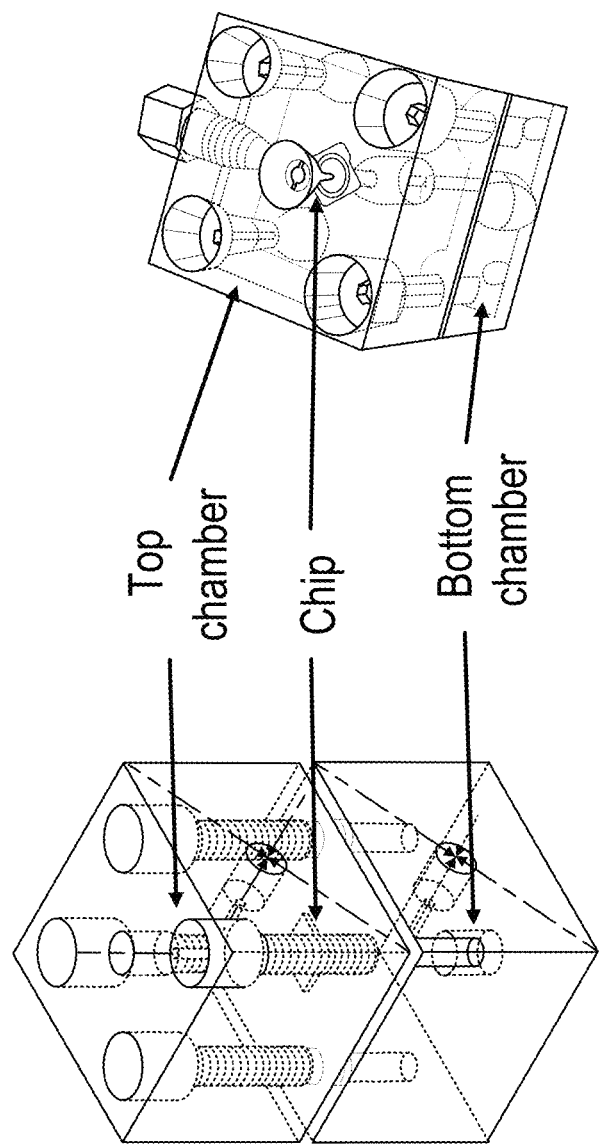

FIG. 5H shows two perspective views of an exemplary nanopore device for analyzing biological molecules according to an embodiment of the present invention. The nanopores on the sapphire substrate in FIG. 5F can be integrated on a silicon integrated circuit chip, which can include control and signal process circuits. Such an integrated nanopore chip can include additional components such as current measuring circuits, control circuits, and signal processing circuits, etc. The integrated chip can be assembled in a fluidic jig, as shown in FIG. 5H. The fluidic jig includes an integrated nanopore device chip containing the nanopore disposed between a top chamber and a bottom chamber. The chip is sealed by two o-rings attached to the top and bottom chambers. In operation, DNA, or other biomolecules, can be loaded into the fluidic jig via the top chamber, and an external voltage bias is applied to drive the biomolecule to pass through the nanopore. The electric current can be monitored to detect the biomolecules.

IV. Anisotropic Etching of Sapphire

Figure 6B:
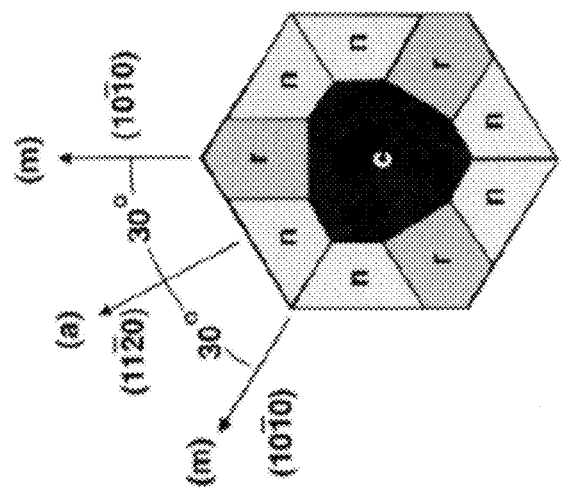
FIG. 6B illustrates a top view of the hexagonal lattice of c-plane sapphire.
Figure 6A:
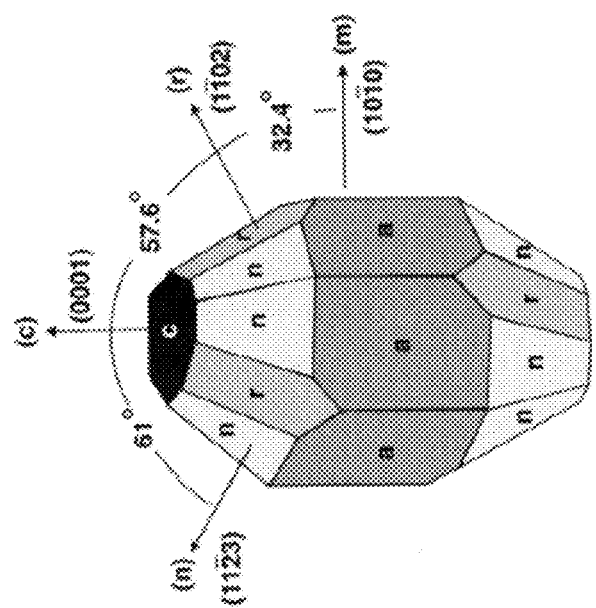
FIG. 6A illustrates a perspective view of a hexagonal lattice of c-plane sapphire.

As described above, in embodiments of the present invention, a method for forming a nanopore device on a sapphire substrate includes anisotropic etching of a sapphire substrate based on different etching rates of various crystalline planes in a sapphire substrate using appropriate wet etching chemicals. FIG. 6A illustrates a perspective view of a hexagonal lattice of c-plane sapphire, and FIG. 6B illustrates a top view of the hexagonal lattice of c-plane sapphire. FIGS. 6A and 6B illustrate various crystalline facets, such as c-plane, a-plane, n-plane, r-plane, etc. As described below, crystalline orientation dependent etching of the sapphire substrate can be used to precisely control the membrane size in the nanopore device structure.

Figure 7A:
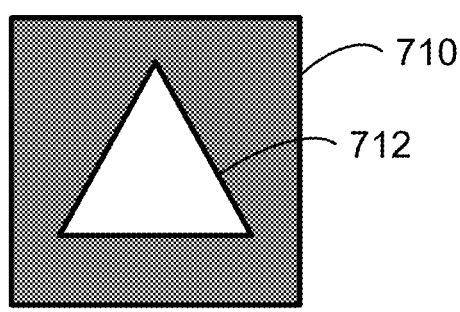
FIGS. 7A-7C illustrate a method of using a triangular-shaped etching mask for forming a triangular-shaped membrane according to some embodiments of the present invention.
Figure 7B:
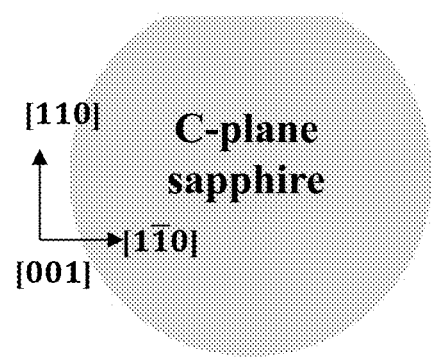
Figure 7C:
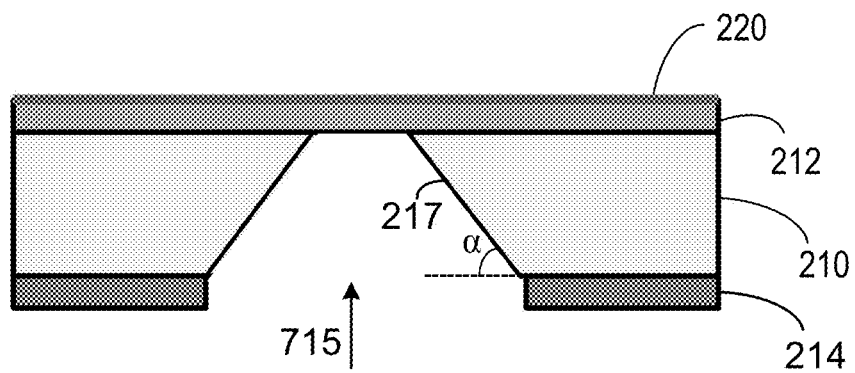

The etching mask can be patterned and aligned to selected crystal orientations of the sapphire substrate for accurate determination of the membrane dimensions. For example, FIGS. 7A-7C illustrate a method of using a triangular-shaped etching mask for forming a triangular-shaped membrane according to some embodiments of the present invention. FIG. 7A illustrates a triangular-shaped etching mask 710 with a triangular opening 712. FIG. 7B illustrates a top view of a c-plane sapphire wafer, which has a top surface in the c-plane. Three crystalline orientations [001], [110], and [110] are also shown.

FIG. 7C is a cross-sectional view illustrating an intermediate structure in the method described above after the sapphire etching process. In FIG. 7C, a sapphire substrate 210 has dielectric layers 212 and 214 disposed on its top and bottom surfaces. A membrane layer 220 is disposed overlying top dielectric layer 212 on the sapphire substrate. As explained above in connection with FIG. 5C, a cavity is formed in sapphire substrate 210 having sidewalls 217, which forms an angle α with a horizontal sapphire surface. As described further below, the angle α is determined by the crystalline orientation dependent etching process.

Figure 7D:
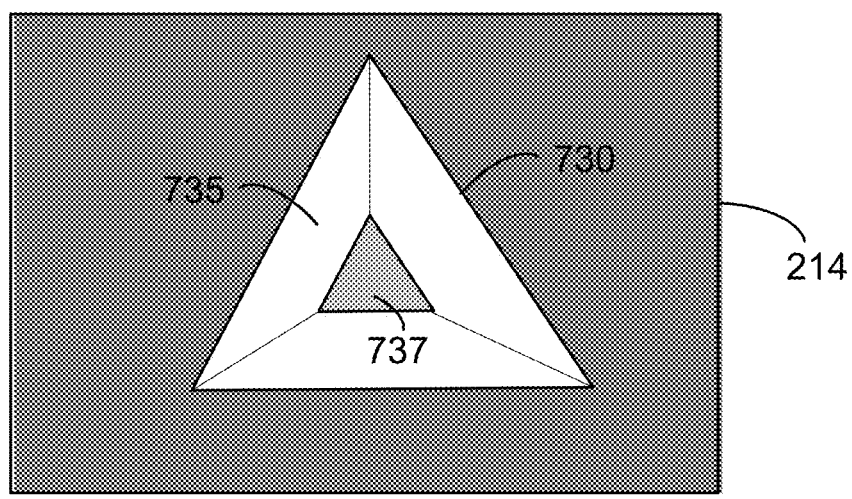

FIG. 7D is a plan view of the device structure in FIG. 7C from the bottom of the sapphire substrate, along the direction of arrow 715. As shown in FIG. 7D, a triangular opening 730 is formed in oxide layer 214 after the oxide layer 214 is etched using a triangular mask, such as mask 710 in FIG. 7A. Sloped sidewalls 735 are etched in the sapphire substrate along crystalline facets that lead to a triangular region 737 in oxide layer 212. In this example, the sides of the triangles in the mask are aligned parallel to or forming 60°/120° angles from [110] direction in the sapphire. As a result, the etching of the sapphire substrate follows the three facets to expose the triangular oxide region. This process provides uniform etching depth control determined by etching along the crystalline facets. Therefore, it is possible to determine the window size of exposed oxide in triangular region 737 based on the size of the triangular opening in the mask layer 710.

V. Determination of Mask Window Size for Sapphire Etching

Figure 8A:
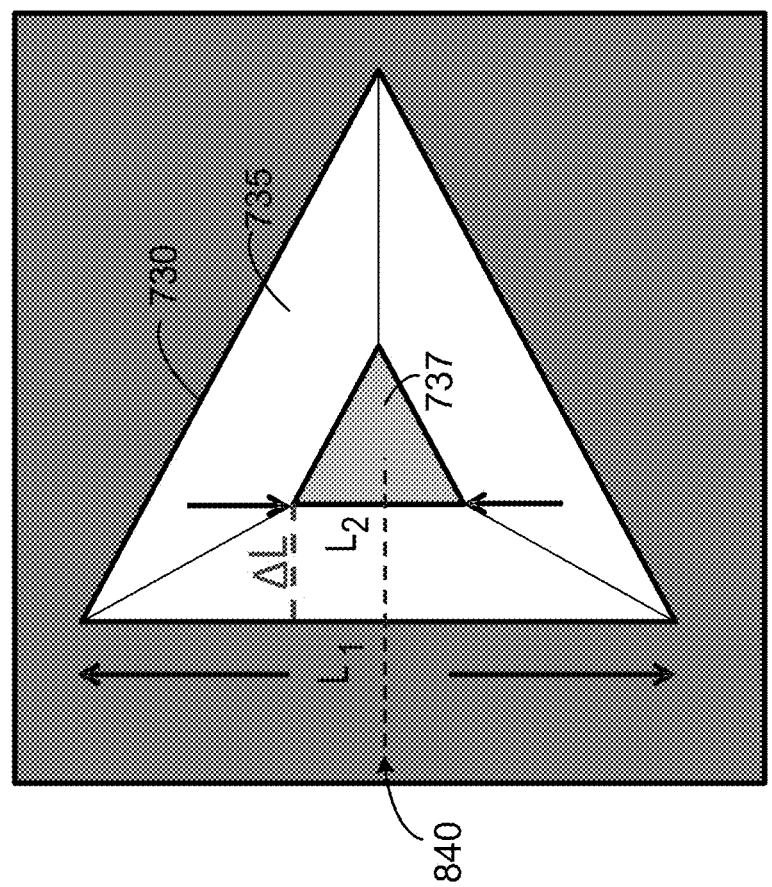
FIGS. 8A and 8B illustrate a method for correlating the triangular-shaped sapphire mask window size to the final membrane window size according to some embodiments of the present invention.
Figure 8B:
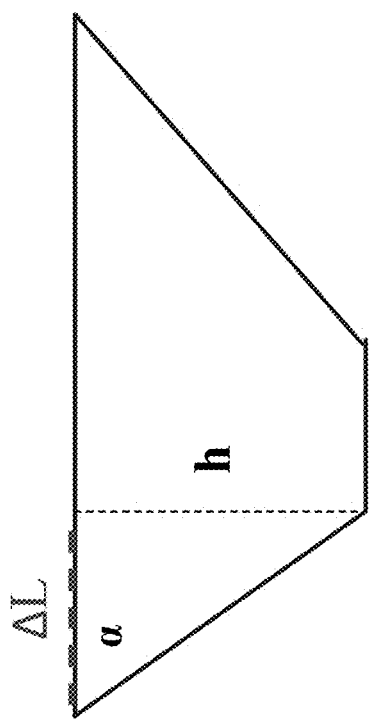

FIGS. 8A and 8B illustrate a method for correlating the triangular-shaped sapphire mask window size to the final membrane window size according to some embodiments of the present invention. This calculation can be used to determine the pattern mask for each customized membrane dimension. FIG. 8A is a top view of an etched cavity in a sapphire substrate, similar to FIG. 7D. Etching the sapphire substrate through the triangular-shaped mask window 730 results in a triangular membrane 737, and the sloped sidewalls 735 are the facets evolved during selective etching.

FIG. 8B is a cross-sectional view along a cut line in FIG. 8A along a dashed line 840. Length $L_1$ is the length of a side of the mask window, and $L_2$ is the length of a side of the final membrane. Then we have the following relationships, $$L_1 = L_2 + 2\sqrt{3}\Delta L$$

$$h/\Delta L = \tan\alpha$$

where α is the angle between the c-plane sapphire and the evolved sidewall facets during etching, and h is the depth of the cavity or the thickness of the sapphire wafer. It follows that the relationship between the etching window sizes can be expressed as follows, $$L_1 = L_2 + 2\sqrt{3}h/\tan\alpha.$$

In the method describe above, the depth of the cavity in the sapphire substrate h is the depth of the cavity and is also the thickness of the sapphire substrate, which typically ranges from 100 μm to 1 mm. After determination of the sapphire thickness to be used and the etching angle α, the length of the side of the window in each mask $L_1$ can be completely determined based on the desired membrane size $L_2$.

Figure 9C:
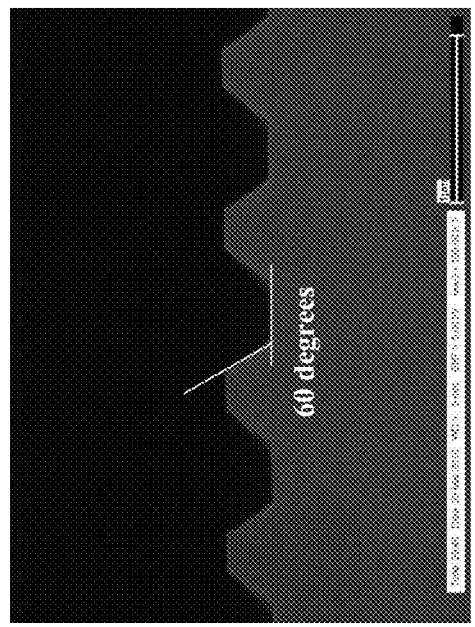
FIGS. 9A-9C illustrate a method for determining the angle α along the etched facets of a sapphire substrate according to some embodiments of the present invention.
Figure 9B:
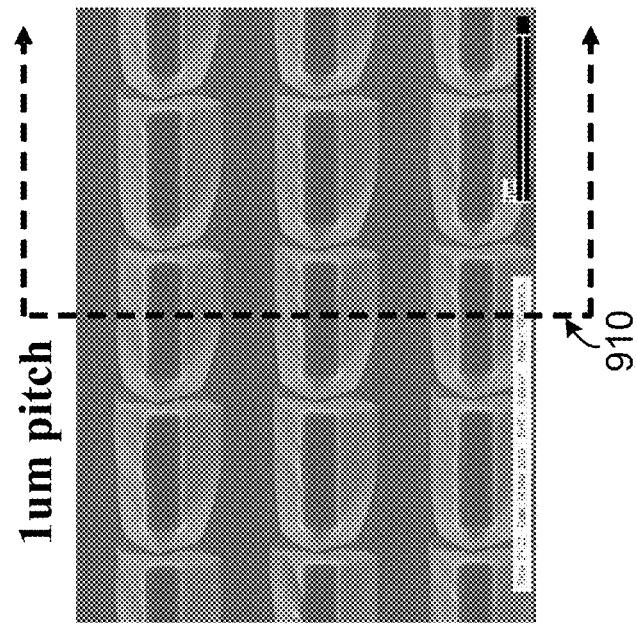
Figure 9A:
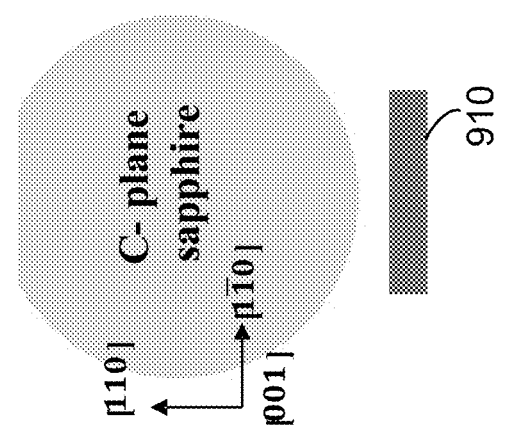

FIGS. 9A-9C illustrate a method for determining the angle α along the etched facets of a sapphire substrate described above according to some embodiments of the present invention. FIG. 9A, similar to FIG. 7B, illustrates a top view of a c-plane sapphire wafer, which has a top surface in the c-plane. Three crystalline orientations [001], [110], and [1̄10] are also shown. FIG. 9A also shows bar-shaped etching mask pattern 910 along the [110] direction in sapphire.

FIG. 9B is a scanning electron microscope (SEM) image showing a top cross-sectional view of the c-plane sapphire after etching a sapphire substrate using a mask having repeated bar shaped patterns. FIG. 9C is a cross-sectional view along the dotted line 960 in FIG. 9B illustrating the c-plane sapphire after etching. It can be seen that multiple trapezoid-shaped structures are formed with a flat top surface defined by the bar-shaped mask and sloped sidewalls crystalline facets as a result of crystalline orientation dependent of selective etching of the sapphire substrate. It can be determined from FIG. 9C that the angle α between a sloped sidewall and a flat bottom surface is about 60 degrees.

Figure 10:
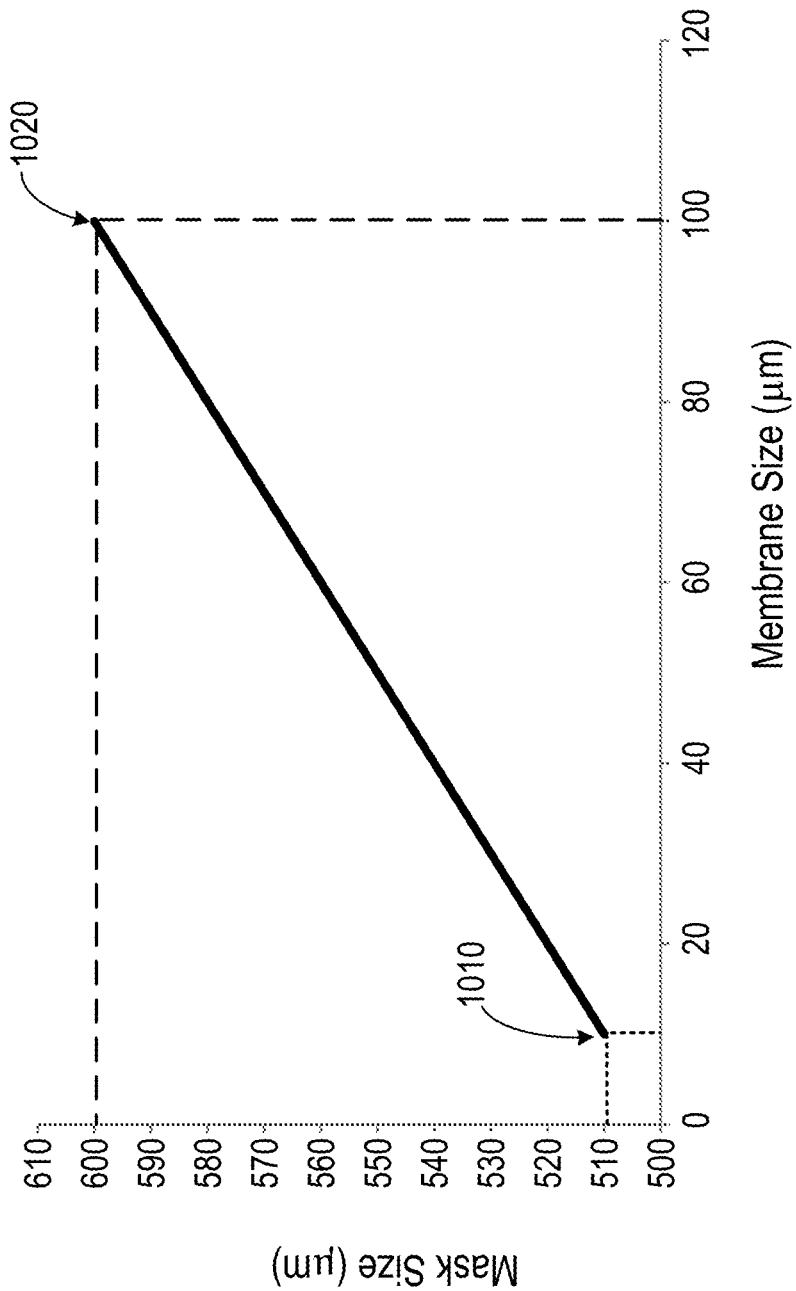
FIG. 10 is a plot illustrating the relationship between the length of mask window and the side length of the final membrane according to some embodiments of the present invention.

FIG. 10 is a plot illustrating the relationship between the length of mask window and the side length of the final membrane according to some embodiments of the present invention. The plot is derived by plotting $L_1$ vs. $L_2$ using the relationship described above, $$L_1 = L_2 + 2\sqrt{3}h/\tan\alpha$$

with α=60° and a sapphire thickness of 250 μm. For example, for a membrane size $L_2$ of about 10 μm, the mask dimension $L_1$ can be determined to be about 510 μm, as indicated by data point 1010. To get a larger membrane size $L_2$ of about 100 μm, the mask dimension $L_1$ can be determined to be around 600 μm, as indicated by data point 1020. This method allows good control of membrane size, which is critical to controlling the membrane capacitance and the current noise.

Wet etching of sapphire substrate also offers additional advantages over dry etching. Dry etching of sapphire substrates is commonly used in light emitting diode (LED) applications. Patterns can be anisotropically etched into the crystalline structure, resulting in a vertical profile. However, dry etching of sapphire is a very slow process with a low throughput rate. It has been reported that dry etching rates range between 50 nm to 200 nm per minute, or 20 minutes per micron. In comparison, the high-temperature wet etching process can be faster and less expensive than dry etching. As described above, during high-temperature wet etching, sapphire wafers are placed in a tank containing a mixture of etching and buffering agents, e.g., sulfuric and phosphoric acids. The etching selectivity between two different crystalline planes can, for example, be 5:1, 10:1, or even 100:1. The rates can be sufficiently different that one crystalline plane may appear not etched relative to another plane. As to the etch rate, the sapphire substrate can be etched at about 0.1 μm to 1 μm per minute such that the cavity in the sapphire substrate can be formed in a reasonable amount of time. In addition, the dry etching tools handles very limited wafers (usually one) at a time; in comparison, the wet-etching process can handle tens or hundreds of wafers at a time, hence significantly improving the throughput.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Where a range of values is provided, it is understood that each intervening value, to the tenth of the unit of the lower limit unless the context clearly dictates otherwise, between the upper and lower limits of that range, is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods Several embodiments of the invention are described above. However, it will be recognized by those of skill in the art that various modifications, alternative constructions, and equivalents may be used without departing from the spirit of the invention. For example, even though a sapphire substrate is used as an example in the above description, other insulating substrates having crystalline orientation dependent etch selectivity can also be used in other embodiments. Moreover, besides silicon nitride, other dielectric materials can also be used to form the membrane, for example, silicon oxide. Additionally, a number of well-known processes and elements have not been described in order to avoid unnecessarily obscuring the present invention. Additionally, details of any specific embodiment may not always be present in variations of that embodiment or may be added to other embodiments.

What is claimed is:

1. A method for forming a nanopore device, comprising:
   providing a sapphire substrate;
   forming a first oxide layer on a front side of the sapphire substrate and a second oxide layer on a back side of the sapphire substrate;
   patterning the second oxide layer on a backside of the sapphire substrate to form an etch mask having a mask opening in the second oxide layer;
   performing a crystalline orientation dependent wet anisotropic etch on the backside of the sapphire substrate using the etch mask to form a cavity having sloped side walls through the sapphire substrate to expose a portion of the first oxide layer, each of the sloped side walls being a crystalline facet aligned with a respective crystalline plane;
   forming a silicon nitride membrane layer on the first oxide layer on the front side of the sapphire substrate;
   removing the exposed portion of the first oxide layer in the cavity to expose a portion of the silicon nitride membrane layer such that the exposed portion of the silicon nitride membrane layer is suspended over the cavity in the sapphire substrate; and
   forming an opening in the exposed portion of the silicon nitride membrane layer to form a nanopore.

2. The method of claim 1, wherein patterning the second oxide layer comprises:
   forming a photoresist layer overlying the second oxide layer on the backside of the sapphire substrate;
   patterning the photoresist layer on the second oxide layer;
   etching the second oxide layer using the patterned photoresist layer as a mask; and
   removing the photoresist layer.

3. The method of claim 1, wherein the mask opening in the etch mask has a polygon shape, each of the sides of the mask opening being aligned with a crystalline plane of the sapphire substrate.

4. The method of claim 1, wherein performing the wet anisotropic etch of the sapphire substrate comprises etching the sapphire substrate using a mixture of sulfuric acid and phosphoric acid at an elevated temperature.

5. The method of claim 1, wherein the silicon nitride membrane layer has a thickness of 5 nm to 50 nm.

6. The method of claim 1, wherein forming an opening in the exposed portion of the silicon nitride membrane layer comprises using nanolithography and RIE (reactive ion etching).

7. The method of claim 1, wherein forming the first and the second oxide layers comprises using a plasma enhanced chemical vapor deposition (PECVD) process.

8. The method of claim 1, wherein a thickness of the first and second oxide layers is in a range of 10 nm to 10 µm.

9. The method of claim 1, wherein both the front side and the back side of the sapphire substrate are characterized by a c-plane orientation.

10. The method of claim 9, wherein the mask opening in the etch mask is a triangular-shaped mask opening, each of three sides of the triangular-shaped mask opening being aligned with a hexagonal crystalline orientation of the sapphire substrate.

11. The method of claim 9, wherein the etch mask has a triangular-shaped mask opening, wherein each of three sides of the triangular-shaped mask opening is aligned parallel to a crystalline plane in the sapphire substrate or forms a 60° or 120° angle from said crystalline plane in the sapphire substrate.

12. A method for forming a nanopore device, comprising:
providing a crystalline insulating substrate having a wet etching selectivity that is crystalline orientation dependent;
forming a first dielectric layer on a front side of the crystalline insulating substrate and a second dielectric layer on a back side of the crystalline insulating substrate;
patterning the second dielectric layer on a backside of the crystalline insulating substrate to form an etch mask having a mask opening in the second dielectric layer;
performing a wet anisotropic etch on the backside of the crystalline insulating substrate using the etch mask to form a cavity that extends through the crystalline insulating substrate to expose a portion of the first dielectric layer;
forming a membrane layer on the first dielectric layer on the front side of the crystalline insulating substrate;
removing the exposed portion of the first dielectric layer in the cavity such that a portion of the membrane layer is suspended over the cavity in the crystalline insulating substrate; and
forming an opening in the suspended portion of the membrane layer to form a nanopore.

13. The method of claim 12, wherein an etching selectivity between two different crystalline planes is greater than 5:1.

14. The method of claim 12, wherein the nanopore has a size that is configured to allow one nucleic acid molecule to pass through the nanopore.

15. The method of claim 12, wherein the cavity has sloped sidewalls through the crystalline insulating substrate to expose a portion of the first dielectric layer.

16. The method of claim 12, wherein the cavity is configured to extend from a first opening in the back side of the crystalline insulating substrate to a second opening in the front side of the crystalline insulating substrate, the second opening being smaller than the first opening, and sidewalls extending from the first opening to the second opening are characterized by crystalline orientations determined by the wet anisotropic etch.

17. The method of claim 12, wherein the crystalline insulating substrate comprises a sapphire substrate.

18. The method of claim 17, wherein the cavity is configured to extend from a first triangular opening in a back side of the sapphire substrate to a second triangular opening in a front side of the sapphire substrate, the second triangular opening being smaller than the first triangular opening.

19. A nanopore device for analyzing biological molecules, the nanopore device comprising:
a nanopore disposed in a membrane suspended over a cavity in a sapphire substrate, wherein the cavity extends from a first triangular opening in a back side of the sapphire substrate to a second triangular opening in a front side of the sapphire substrate, wherein the first triangular opening and the second triangular opening are triangular in shape in a plan view from the back side of the sapphire substrate, the second triangular opening being smaller than the first triangular opening;
a first fluidic reservoir and a second fluidic reservoir fluidically coupled to the nanopore;
first and second electrodes coupled to an electrically conductive fluid disposed in the first fluidic reservoir and the second fluidic reservoir, respectively; and
an electrical measuring device for measuring an electrical signal between the first and second electrodes.

20. The nanopore device of claim 19, wherein the nanopore device is configured to apply an electrical voltage between the first and second electrodes and measure a current signal between the first and second electrodes.

21. The nanopore device of claim 19, wherein the nanopore device is configured to apply an electrical current between the first and second electrodes and measure a voltage signal between the first and second electrodes.

22. The nanopore device of claim 19, wherein the cavity is formed by a wet anisotropic etch of the sapphire substrate using a mask having a triangular-shaped mask opening, and each of three sides of the triangular-shaped mask opening is aligned with a hexagonal crystalline orientation of the sapphire substrate.

23. The nanopore device of claim 19, further comprising a dielectric layer disposed on side surfaces of the cavity in the sapphire substrate.

24. The nanopore device of claim 19, wherein the front side and the back side of the sapphire substrate are configured in c-planes of the sapphire substrate, and the first triangular opening in the back side of the sapphire substrate has three sides, each side being aligned with a hexagonal crystalline orientation of the sapphire substrate.

25. The nanopore device of claim 19, wherein the sidewalls connecting the first opening and the second opening are characterized by crystalline orientations determined by a wet anisotropic etch.

* * * * *